(12) United States Patent
Xie et al.

(10) Patent No.: US 8,701,879 B2
(45) Date of Patent: *Apr. 22, 2014

(54) FRANGIBLE CAPSULE-IN-CAPSULE CHEMICAL DELIVERY SYSTEMS AND METHODS OF FABRICATION

(75) Inventors: Tao Xie, Troy, MI (US); Anil K. Sachdev, Rochester Hills, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 933 days.

This patent is subject to a terminal disclaimer.

(21) Appl. No.: 12/687,193

(22) Filed: Jan. 14, 2010

(65) Prior Publication Data
US 2011/0062036 A1   Mar. 17, 2011

Related U.S. Application Data

(60) Provisional application No. 61/241,475, filed on Sep. 11, 2009.

(51) Int. Cl.
| | | |
|---|---|---|
| *B65D 25/08* | (2006.01) | |
| *B65B 29/10* | (2006.01) | |
| *B32B 9/02* | (2006.01) | |

(52) U.S. Cl.
USPC ........... 206/222; 424/451; 424/458; 428/402; 428/402.2; 53/474

(58) Field of Classification Search
USPC ....... 206/222, 234; 53/474; 29/428; 424/493, 424/497, 451; 435/325, 40.5, 283.1, 307.1; 428/697, 402–402.24, 407, 403, 423.1, 428/474.4; 427/389.9, 213.3–213.36
See application file for complete search history.

(56) References Cited

U.S. PATENT DOCUMENTS

| | | | |
|---|---|---|---|
| 6,709,673 B1 * | 3/2004 | Tebbe ........................... | 424/451 |
| 2004/0020568 A1 * | 2/2004 | Phelps et al. .................. | 148/273 |
| 2006/0073334 A1 * | 4/2006 | Schwantes et al. ........ | 428/402.2 |
| 2007/0003631 A1 * | 1/2007 | Sayre et al. .................... | 424/490 |

* cited by examiner

*Primary Examiner* — James J Seidleck
*Assistant Examiner* — S. Camilla Pourbohloul
(74) *Attorney, Agent, or Firm* — Reising Ethington P.C.

(57) ABSTRACT

A capsule-in-capsule system comprising at least two segregated chemical reactants is described. An inner capsule contains one reactant and is itself contained, with a second chemical reactant, in an outer capsule. The inner capsule and its contents is fabricated first; then it is incorporated into the second reactant; and the combination of the second reactant and inner capsule is encapsulated in the outer capsule. The reactants may be hydrophobic or hydrophilic and present as fluids, solids or combinations of solid(s) and fluids(s). When subjected to suitably high pressure, the capsule wall materials will fracture or rupture, releasing and preferably mixing all encapsulates to enable their prompt reaction. The utility of the invention is illustrated by its application to development of a corrosion inhibiting passive film on magnesium auto body material and to the adhesive bonding of members where precise positioning is desired.

8 Claims, 2 Drawing Sheets

FRANGIBLE CAPSULE-IN-CAPSULE CHEMICAL DELIVERY SYSTEMS AND METHODS OF FABRICATION

This application claims priority of U.S. Provisional Application Ser. No. 61/241,475, filed on Sep. 11, 2009.

TECHNICAL FIELD

The present invention relates to the development and application of capsule-in-capsule structures, where a relatively smaller capsule containing a first chemical material is contained within a larger capsule that also contains a second chemical material enveloping the smaller capsule. The first and second chemical materials may be exposed to one another upon fracture or rupture of both capsules.

BACKGROUND OF THE INVENTION

There are pharmaceutical manufacturing applications in which dosage amounts of medicines are encapsulated in relatively stable gelatin-containing shells known as capsules. The capsules may be taken orally whereby the shell is dissolved and the medicine assimilated into the body. It is also understood that carbonless copy paper is coated with microcapsules containing a dye. When someone writes on the sheet the microcapsule breaks to spill the dye. These are examples of the use of individual capsules to contain a chemical material that is secured until the capsule shell is broken or otherwise removed in an intended site of use.

It is an object of this invention to provide frangible shelled capsules which themselves comprise inner capsules with frangible shells, each shell separately containing different chemical materials that are capable of interacting when their enclosing shells are broken or otherwise penetrated.

SUMMARY OF THE INVENTION

The invention seeks to separably incorporate multiple chemical species in separate inner and outer shells. This is achieved by use of a structure comprising an outer capsule enclosing both at least a first chemical species and at least one inner capsule within its enclosed volume. The capsule walls or shells of each capsule are selected to be impermeable to all external or internal chemical species they may encounter. Thus, the chemical species are maintained separate and isolated from the local environment while the outer and inner capsules are intact but will at least be brought into contact with one another and preferably intermingle when the capsules are ruptured or fractured. The chemical species may also react with one another or one of the species may catalyze reaction in a species capable of undergoing reaction or transformation, such as polymerization, when the rate of such reaction is suitably enhanced. The interactive chemical species may be adapted to perform many desired results including, among others, the formation of a corrosion protection layer on a metal surface and the in-situ formation of an adhesive.

The invention generally provides for a first relatively large outer capsule which encloses a segregated first chemical species and a smaller inner capsule which encloses a second chemical species. The overall structure is of an encapsulated first chemical species generally surrounding a second encapsulated chemical species. Either species may be present as a liquid or as a solid and the encapsulating materials are selected to be non-reactive both with the contents of the capsule and with their intended local external environment.

It is preferred that the capsule walls or shells surrounding the first and second chemical species be of comparable strength so that rupture of one capsule will be accompanied by rupture of the second capsule. However, the chemical composition or thickness of the capsule shells, which will generally comprise a carbon-based polymer, may result in markedly different shell strengths. In either event, the fracture of one capsule should be accompanied by the fracture of the second capsule. One means of achieving this goal is to have the stronger capsule enclose the weaker capsule. The utility of the invention is that it conveys chemical reactants capable of imparting desired attributes to an article of manufacture at pre-determined locations. Thus the strength and size of the capsules may be adapted for placement in the environment in which they are intended to operate.

The size of the outer capsules often depend on the site at which they are to be used and the relative sizes of the outer and inner capsules often depend on the amounts of the respective materials they are to contain. Quantities of the chemical species may be suitably proportioned for their intended function. As stated, such a required proportionality may affect the relative sizes of the outer and inner capsule layers. Thus, for example, where chemical reaction is intended, the species will normally be present in molar ratio suitable for the chemical reaction. Similarly, if molar excess of one constituent is desired for reaction kinetic or other purposes, the molar ratio and the relative outer and inner capsule sizes may be adjusted accordingly. In some circumstances, polymerization promoted by a catalyst for example, only minimal quantities of a second species may be required.

In a first embodiment, the first chemical species is a fluid encapsulated in a first capsule, the first capsule being at least partially surrounded by a second fluid chemical species encapsulated in a second capsule wherein the first capsule is wholly contained within the second capsule. As used herein, fluids may comprise homogeneous liquids or solutions, emulsions or solid-liquid dispersions.

In a second embodiment, the first chemical species is a solid encapsulated in a first capsule, the first capsule being at least partially surrounded by a second fluid chemical species encapsulated in a second capsule wherein the first capsule is wholly contained within the second capsule.

In a third embodiment, the first chemical species is a fluid encapsulated in a first capsule, the first capsule being at least partially surrounded by a second solid chemical species encapsulated in a first microcapsule wherein the first capsule is wholly contained within the second capsule.

In a fourth embodiment a first chemical species is a solid incorporated in a first capsule, the first capsule being at least partially surrounded by a second solid chemical species encapsulated in a second capsule wherein the first capsule is wholly contained within the second capsule.

The shapes of the capsules may, for example, be ellipsoidal, spherical, cylindrical with rounded ends, irregular, or as otherwise needed for an intended application. It is anticipated that mechanical pressure will be the most common method of initiating capsule rupture, but the invention also comprehends that other stimuli such as vibration or electromagnetic radiation or magnetic fields may be employed. Such approaches are intended to induce heating in the capsules and thereby promote, by vaporization or decomposition of the contents an internal pressure sufficient for capsule rupture. Additional elements, such as carbon nanotubes or magnetic particles may be incorporated in the capsule to promote more effective coupling of the radiation to the capsule.

It will be understood that the term capsule is not intended to limit the size of the entrained volume of chemical species.

Thus the terms 'capsule' or 'capsules' is intended to comprehend not only capsules whose dimensions are expressed in millimeters but also capsules with dimensions of micrometers, frequently called micro-capsules, as well as capsules with dimensions of nanometers, frequently called nano-capsules.

Other objects and advantages of the invention will be apparent from a description of illustrative embodiments which follows in this specification and refers to the following drawing figures.

DESCRIPTION OF PREFERRED EMBODIMENTS

Encapsulation and, more specifically, micro-encapsulation methods may be broadly subdivided into chemical and mechanical approaches. Chemical approaches include: complex coacervation; polymer incompatibility; interfacial polymerization in liquid media; in situ polymerization; in-liquid drying; thermal and ionic gelation in liquid media; and desolvation in liquid media. Mechanical methods include: spray drying; spray chilling; fluidized bed (Wurster coating); electrostatic deposition; centrifugal extrusion; spinning disc or rotational suspension separation; polymerization at liquid-gas or solid gas interface; and pressure spraying or extrusion into a solvent extraction bath.

Application of all or some of the approaches listed is comprehended in practice of this invention.

It will be recognized that the selection of a suitable process will be informed by the physical character of the encapsulate, liquid or solid, and by its chemical character which may promote or prejudice specific processes. It will further be recognized that the size of the capsules obtainable with different encapsulation processes may vary both by process and by practice of the process. For example, capsules ranging in diameter from 20 to 800 micrometers may be readily produced using complex coacervation while interfacial polymerization more typically yields particles of 20 to 30 micrometers. Capsule shell thicknesses may be adjusted over wide ranges but are generally related to the capsule diameter. Shell thicknesses most commonly adopt values ranging from 5% to 10% of the capsule diameter.

For some applications, for example where the capsules are to be unobtrusively incorporated in a thin layer, a paint layer for instance, which itself is only 20 to 30 micrometers thick, the ability of a process to produce small capsules may be the primary factor dictating process choice. In yet other applications where size constraints are minimal it may be preferred to use larger capsules, each capable of more efficiently containing a larger individual volume of chemical species.

Size considerations may be yet more significant in practice of this invention because it comprehends at least two encapsulation processes: a first process to encapsulate a first reactant and an at least second process to encapsulate a second reactant incorporating the first capsule as shown in FIGS. 1-4.

Figure 1:
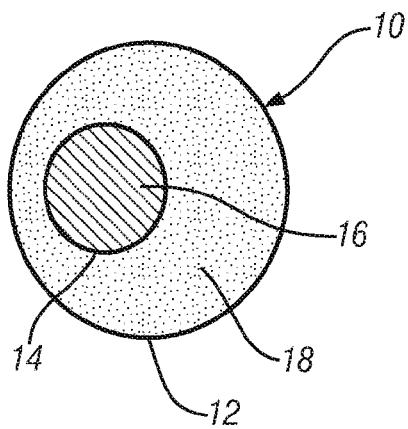
FIG. 1 shows in cross-section (and enlarged for clear illustration) a first embodiment of the invention, in which a first generally ellipsoidal (or spherical) liquid-containing capsule is contained within a second, generally ellipsoidal or spherical liquid-containing capsule.

FIG. 1 shows a first embodiment in which both reactants are liquid. FIG. 1 shows a capsule-in-capsule structure 10 comprising a first liquid chemical species 16 enclosed by a capsule shell 14, capsule shell 14 being generally surrounded by a second capsule shell 12, capsule shell 12 further enclosing second liquid chemical species 18. In this and the following figures the relative sizes of the respective capsule shells are predetermined for the application site and the relative amounts of the encapsulated constituent materials for the application.

Figure 2:
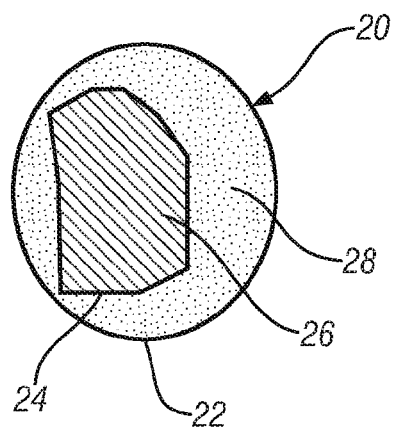
FIG. 2 shows in cross-section (and enlarged for clear illustration) a second embodiment of the invention in which a first irregularly-shaped solid-containing capsule is contained within a second, generally ellipsoidal liquid-containing capsule.

FIG. 2 shows a second embodiment in which a capsule-in-capsule structure 20 comprises a solid chemical species 26 enclosed by capsule shell 24, capsule shell 24 being generally surrounded by a second capsule shell 22 enclosing liquid second chemical species 28.

Figure 3:
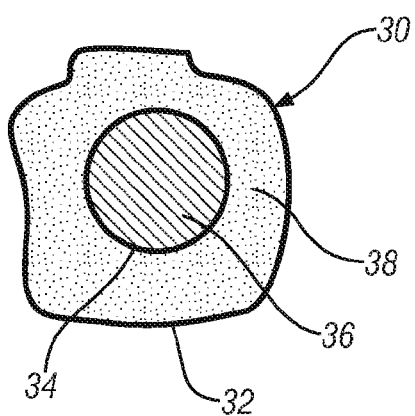
FIG. 3 shows in cross-section (and enlarged for clear illustration) a third embodiment of the invention in which a first generally spheroidal liquid-containing capsule is contained within a second, generally irregularly-shaped solid-containing capsule.

FIG. 3 shows a third embodiment in which a capsule-in-capsule structure 30 comprises a liquid chemical species 36 and enclosed by capsule shell 34, is generally surrounded by a second capsule shell 32 enclosing solid second chemical species 38.

Figure 4:
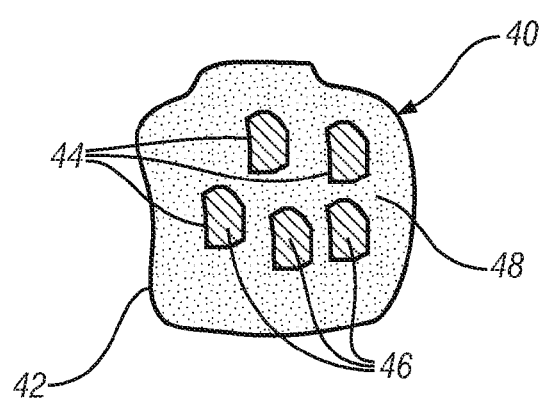
FIG. 4 shows in cross-section (and enlarged for clear illustration) a fourth embodiment of the invention in which a first irregularly-shaped solid-containing capsules are contained within a second, generally irregularly-shaped solid-containing capsule.

Finally, FIG. 4 shows a fourth embodiment in which a capsule-in-capsule structure 40 comprises a solid chemical species 48 enclosed by capsule shell 42, generally surrounds a plurality of second capsule shells 44 enclosing solid second chemical species 46.

From consideration of the figures and accompanying description it will be appreciated that application of mechanical loads sufficient to fracture all shells depicted in FIGS. 1-4 will simultaneously expose both chemical species to one another, in pre-selected proportion and at near-identical location. Thus the issues identified with the use of multiple single-species capsules containing different species have been overcome.

It will be further appreciated that the invention may be readily extended to the use of additional species and additional capsule layers without prejudice to the benefits obtained with the illustrated two-species configuration.

The benefits and advantages of the invention may be further appreciated by consideration of the following examples directed to imparting local corrosion protection to painted magnesium body panels in an automobile and development of a repositionable or on-demand fast-setting two part adhesive.

Example 1

Automotive paint satisfies both an aesthetic and a functional requirement. Functionally the paint acts as a barrier layer which restricts access of the frequently corrosive operating environment encountered by automobiles to the underlying metallic body and thereby acts to suppress corrosion of the body. When the paint is damaged to an extent sufficient to expose the underlying metal surface to the environment, corrosion of the metal surface may be anticipated, unless the paint layer is repaired. Preferably such repair should be undertaken promptly and more preferably should be accomplished before any corrosion has occurred. However the operating environment experienced by automobiles coupled with the delays occurring between occurrence, detection and repair of such damage makes it almost inevitable that an unprotected metal surface will undergo at least some corrosion before remedial action is taken. Thus a means of at least temporarily preventing or delaying corrosion of metal automotive body panels when paint is damaged sufficiently to expose the underlying metal surface is sought.

Figure 5:
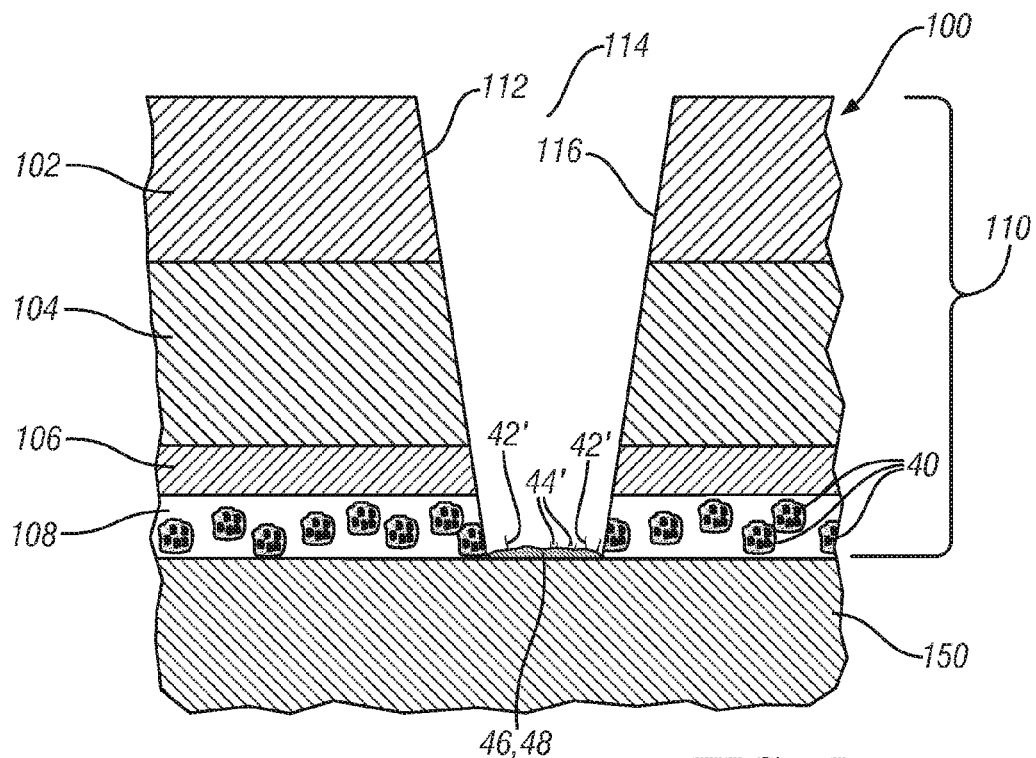
FIG. 5 is a fragmentary view, in cross-section, showing an exemplary embodiment of the invention in which a series of multi-layer capsules have been incorporated in one of a series of paint layers such as are employed on an automobile body. In this example the capsules have been dispersed in the paint layer adjacent to the surface of a metallic body panel.

Although collectively known as paint, automobile body finishes comprise multiple layers as illustrated in fragmentary view 100 of paint on a magnesium panel 150 in FIG. 5. Here 'paint' shown as 110 comprises four layers: a clear coat 102; a topcoat 104; a primer-surfacer 106; and, immediately adjacent to the magnesium panel 150, an electrodeposited coating 108. In this instance the electrodeposited coating 108 has been modified to incorporate suitably-sized solid-solid capsule-in-capsule structures 40 with features and constituents as depicted in FIG. 4. In this figure, the paint layers are shown as damaged at location 114, the damage having resulted in the removal of all paint 110 in the region bounded by surfaces 112 and 116. A further result of the damage has been the fracture of some of capsule-in-capsule structures 40 leading to the release and comingling of the capsule contents 46,48 and leaving behind capsule shell fragments 42' and 44'.

It is well known that particular combinations of chemicals, in an aqueous solution and in contact with a metallic surface will react with that surface to form a 'conversion layer' which is effective in at least slowing corrosion reactions. For example, several different conversion coatings, based on chromates, stannates or cerium oxide are effective in reducing corrosion in magnesium alloys but all of these coatings require that more than one chemical species be present in aqueous solution. A specific and effective combination is $Ce_2O_3$ and $NaNO_2$, both of which are solids but beneficially, $NaNO_2$ deliquesces, helping to ensure that an aqueous solution will form if $Ce_2O_3$ and $NaNO_2$ are exposed to moisture or humidity. However $Ce_2O_3$ and $NaNO_2$ will react with themselves even in the absence of magnesium and thus, to be effective in forming a conversion layer on magnesium must be separately stored until needed.

Hence by co-locating $Ce_2O_3$ and $NaNO_2$ in a capsule-in-capsule structure 40 as depicted in FIG. 4 and incorporating these in a suitable concentration in the paint layer closest to the metal, in this case the electrodeposited layer 108, as shown in FIG. 5, $Ce_2O_3$ and $NaNO_2$ may be co-located but temporarily sequestered. However in the event of damage to the paint layers sufficient to expose the magnesium panel, as at location 114, at least some of the multilayered capsules 40 will rupture exposing the $Ce_2O_3$ and $NaNO_2$ (represented in FIG. 5 by comingled capsule contents 46,48) which after absorption of water will react with the exposed magnesium surface to develop a conversion layer.

Electrodeposited layer 108 (FIG. 5) is typically about 30 micrometers thick. Thus the capsule-in-capsule structures 40 should be of some lesser size. Two suitable approaches utilize supercritical processing or dispersion polymerization.

Particles of 10 to 15 micrometers in size may be formed by mechanical methods such as ball milling or by using supercritical fluid processing as is well-known in the art. Similarly, supercritical fluid aided coating is capable of imparting very thin, fractions of a micrometer in thickness, coating layers on particles. Generally the preferred solvent for such supercritical fluid processing is carbon dioxide although propane and nitrous oxide may also be used. A variety of polymer coatings may be employed including polystyrene. Alternatively prepolymer precursors such as styrene, acrylic or vinyl compounds may be used in combination with a suitable chemical initiator or exposure to UV light to induce polymerization.

Dispersion polymerization is also a potential coating process. In this process a carrier fluid is a solvent for a monomer but not its polymer. Thus by suspending and agitating particles in a solvent/monomer solution and adding an initiator to promote polymerization a polymer shell builds on the particles. Polymer shell thicknesses of as little as 50 nanometers have been demonstrated.

The overall process for fabrication of capsule-in-capsule structures would call for a first coating process directed to one of the chemical species followed by a second coating process directed to the second chemical species in combination with the first, now-coated, chemical species. Appropriate particle sizes or size distributions of each of the chemical species particles will be selected to achieve appropriate molar ratios of the species and the coatings selected will ensure the stability of the first coating during the second coating process.

When it is preferred to form aqueous solutions of the chemical species emulsion polymerization methods, as an example, may be used to make sub-micron sized capsules. In such case, the shell material can be made of any monomers suitable for emulsion polymerization including various polymethacrylates, polyacrylates, polystyrene. The polymer shell may be cross-linked when a cross-linker is employed during the emulsion polymerization.

For instance, a saturated water solution of $Ce_2O_3$ may be added to a hydrophobic media (oil phase) in combination with a polymerizable surfactant and a radical initiator. Vigorous agitation of the mixture, aided by the presence of the surfactant will promote formation of an emulsion comprising small droplets of the $Ce_2O_3$ solution coated with a layer of surfactant dispersed in the hydrophobic phase. When heated to about 80° C. the radical initiator will trigger polymerization of the surfactant leading to the development of polymer-encapsulated $Ce_2O_3$. The capsule shells may be cross-linked by including a cross linking species in the mix. The surfaces of the polymer capsules are then treated to render them hydrophilic via plasma treatment for instance.

A similar procedure will result in the desired capsule-in-capsule structure. The first set of $Ce_2O_3$-containing hydrophilic polymer capsules are dispersed in oil to which a saturated water solution of $NaNO_2$ solution and a second polymerizable surfactant are added. This mixture, on appropriate agitation, forms a second water-in-oil emulsion with the water phase containing the first hydrophilic polymer capsules and the $NaNO_2$ water solution. Upon polymerizing the second surfactant, double-layered capsules containing $NaNO_2$ and $Ce_2O_3$ separately are obtained.

Example 2

Two-part adhesives formed by the reaction of two components find broad application. Although the best known example may be 'epoxy' formed by reaction of an epoxide resin and a polyamine hardener, polyurea formed by reaction of isocyanate and polyamines and polyurethane formed by reaction of isocyanates with polyols are also in common use. However in industrial practice isocyanates are almost universally reacted with the slower-reacting polyols to allow sufficient working time for the adhesive. This provides an operator sufficient time to adjust and position the parts to be bonded before the adhesive sets up and bonds the parts together.

Using separately co-located isocyanates and polyamines in capsule form as comprehended by this invention would enable use of a quick-setting polyurethane adhesive capable of easy repositioning just prior to triggering the instant adhesive bond.

Coating one surface to be joined with a layer of such capsules as shown in would enable fit-up of the parts to be joined and afford opportunity for relocating the parts until a sufficiently high load was applied to rupture the capsules, allowing the isocyanate and polyamine to react and adhesively bond the parts together. This would afford adequate time for part fit-up while still producing a strong bond without a need for prolonged clamping during adhesive 'cure'. Effectively this would increase the working time of the adhesive while retaining the bond strength advantages of this formulation.

Figure 6A:
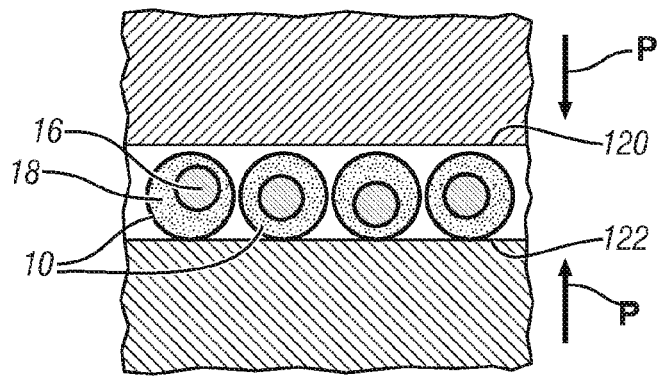
FIG. 6A shows a fragmentary view of two surfaces, one of which is partially covered with capsule-in-capsule structures, each capsule containing one part of a two-part adhesive.
Figure 6B:
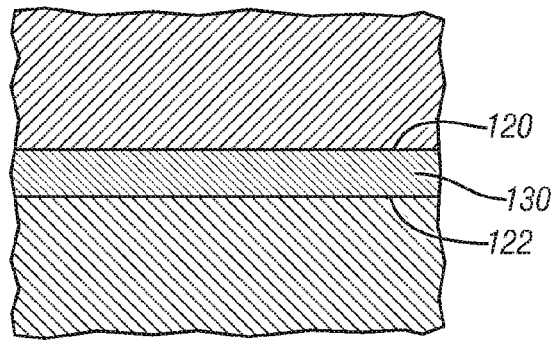
In FIG. 6B, the two surfaces have been forced together under a pressure P, fracturing the capsules and mixing their contents to form an adhesive which bonds the surfaces to one another.

An example of this approach is illustrated in FIGS. 6A and 6B. FIG. 6A shows fragmentary views of surfaces 120 and 122, where surface 122 is at least partially covered with capsule-in-capsule structures 10. Each capsule-in-capsule structure contains, as better shown at FIG. 1, liquid or flowable chemical species 16 and 18 which comprise the constituent species of a two-part adhesive. Under application of pressure P, the surfaces are brought together, rupturing the capsules to release and mix their contents and to enable their reaction to form adhesive 130 to bond the surfaces together as shown in FIG. 6B.

As shown, only gravity retains the capsule-in-capsule structures on surface 122. It is recognized that there may be joint configurations where other methods of temporarily locating the capsule-in-capsule structures on the surface are required. If the surfaces are non-metallic, it may be feasible to exploit electrostatic attraction between surface and capsule. A more general approach, feasible for surfaces of all characters, would be to apply a tacky or mildly-adhesive chemically-compatible coating either to surface 122 or to structures 10 to temporarily locate and secure the capsule-in-capsule structures to the surface.

As an example of such an application, a hydrophilic diamine (e.g. Jaffamine D-2000) may be added to a hydrophobic media (oil phase) in combination with a polymerizable surfactant and a radical initiator. Vigorous agitation of the mixture, aided by the presence of the surfactant will promote formation of an emulsion comprising small droplets of the diamine coated with a layer of surfactant dispersed in the hydrophobic phase. When heated to about 80° C., the radical initiator will trigger polymerization of the surfactant, leading to the development of polymer-encapsulated diamine. The capsule shells may be cross-linked by including a cross linking species in the mix. A hydrophobic diisocyanate compound is dispersed in aqueous solution along with the encapsulated diamine, a polymerizable surfactant, and a radical initiator. Under suitable agitation, emulsion is formed with the preformed capsules surrounded by the diisocyanate, which is further surrounded by the polymerizable surfactant. Upon polymerization of the surfactant, the desired double layered capsules may be formed.

In these examples capsule rupture resulted from direct application of a large mechanical load. However small amplitude vibratory motions such as are developed ultrasonically may also be employed. Further it may be desirable to initiate capsule rupture indirectly, for example by exposing the capsule to a suitable stimulus, for example electromagnetic radiation such as x-rays, microwaves, ultraviolet, visible or infrared light. The choice of stimulus will be dictated by its need to efficiently couple to the capsule-in-capsule structure to promote heating and vaporize the capsule contents (if liquid) or decompose the capsule contents and evolve gas (if solid or liquid). The intent being to generate sufficient internal pressure to exceed the rupture strength of the capsule wall, releasing the capsule contents and permitting them to react.

It may be advantageous to incorporate species, either as a separate encapsulate or in combination with another encapsulate, to promote more effective coupling between the external stimulus and the capsule. For example, absorbing species, such as carbon nanotubes, may be introduced into the capsule to enhance its ability to absorb optical or microwave irradiation. Yet further selectivity may be imparted by 'tuning' the absorbing characteristics by controlling the species' dimensions. Here, capsule rupture could be initiated by exposure to radiation of suitable wavelength and intensity for heating the coupling species which then transfers heat to the contents of the capsule until sufficient pressure is generated to rupture the capsule. A microwave oven or an infra-red laser might be suitable sources of radiation. A yet further example could involve the introduction of species, such as $Fe_3O_4$, which are magnetic followed by exposure to rapidly-oscillating magnetic fields may again promote internal heating in the capsule, leading to pressure build-up and capsule rupture.

Although the utility of this invention has been illustrated by specific applications it should be understood that the detailed description and specific examples, while disclosing exemplary embodiments of the invention, are intended to be illustrative of the invention and are not intended to limit its scope.

The invention claimed is:

1. A capsule-in-capsule structure comprising a closed outer capsule with a closed outer frangible capsule shell and a closed inner capsule with a closed inner frangible capsule shell, the closed inner capsule shell containing a first reactant and the closed outer capsule shell containing a second reactant and the closed inner capsule, the first and second capsule shells being adapted to hold separate the first and second reactants; wherein
 a rupture-producing event suitable for rupturing of one or other of the outer or inner capsules will also immediately rupture the other of the outer or inner capsules; and
 the first reactant is $Ce_2O_3$, as a solid, and the second reactant is $NaNO_2$, as a solid, and at least one of the first and second reactants, upon release, absorbs water when exposed to moisture or humidity, to thereby form an aqueous solution for chemical reaction with a magnesium alloy to form a conversion coating on the magnesium alloy; and
 the size of the outer capsule is adapted for incorporation in a paint film applied to a magnesium article of manufacture.

2. The capsule-in-capsule structure of claim 1 wherein rupture of the inner and outer capsule shells results from application of a force.

3. The capsule-in-capsule structure of claim 1 wherein rupture of the inner and outer capsule shells results from development of internal pressure resulting from heating induced by exposure to electromagnetic radiation.

4. The capsule-in-capsule structure of claim 3 wherein the inner and outer capsules further comprise species adapted to absorb electromagnetic radiation.

5. The capsule-in-capsule structure of claim 4 wherein the energy-absorbing species comprises carbon nanotubes.

6. The capsule-in-capsule structure of claim 2 in which the inner and outer capsules are of comparable strength.

7. The capsule-in-capsule structure of claim 2 in which the outer capsule is stronger than the inner capsule.

8. A capsule-in-capsule structure comprising a closed outer capsule with a closed outer frangible capsule shell and a closed inner capsule with a closed inner frangible capsule shell, the closed inner capsule shell containing a first reactant and the closed outer capsule shell containing a second reactant, suitable for reaction with the first reactant, and the closed inner capsule, the first and second capsule shells being adapted to hold separate the first and second reactants; wherein
  a rupture-producing event suitable for rupturing of one or other of the outer or inner capsules will also immediately rupture the other of the outer or inner capsules to thereby release the contents of the inner and outer capsules and enable reactive contact between first and second chemical species immediately following rupture; and wherein
  the first chemical species is isocyanate and the second chemical species is a polyamine, the first and second chemical species reacting to form a polyurea adhesive, wherein the outer capsule composition is adapted to adhere to an adhesive layer applied to a bonding surface of a first for adhesively joining the first article to a second article when the capsule-in-capsule structure experiences the rupture-producing event.

* * * * *